United States Patent [19]

Thompson

[11] 4,391,598

[45] Jul. 5, 1983

[54] INTRAVENOUS DRUG ADDITIVE DELIVERY SYSTEM WITH ELECTRONIC CONTROL

[75] Inventor: Thomas C. Thompson, McKinney, Tex.

[73] Assignee: Quest Medical, Inc., Carrollton, Tex.

[21] Appl. No.: 258,361

[22] Filed: Apr. 28, 1981

[51] Int. Cl.³ .............................................. A61M 5/00
[52] U.S. Cl. ...................................... 604/65; 604/81; 128/DIG. 13
[58] Field of Search ........... 128/214 R, 214 E, 214 F, 128/214.2, DIG. 12, DIG. 13; 222/145, 426, 428, 450; 604/65, 67, 81, 83

[56] References Cited

U.S. PATENT DOCUMENTS

| | | | |
|---|---|---|---|
| 4,191,184 | 3/1980 | Carlisle | 128/214 E |
| 4,204,538 | 5/1980 | Cannon | 128/214 R |
| 4,207,871 | 6/1980 | Jenkins | 128/214 F X |
| 4,261,356 | 4/1981 | Turner et al. | 128/214 R |
| 4,265,240 | 5/1981 | Jenkins | 128/214 E |
| 4,316,460 | 2/1982 | Genese et al. | 128/214 R |
| 4,324,238 | 4/1982 | Genese et al. | 128/214 G |

OTHER PUBLICATIONS

"New Concepts in Intermittent I.V. Therapy", by Travenol Lab., Inc.
"Life Care Pump Tips", (2 & 6) by Abbott Labs.
"Design Goal: Simple Perfection in I.V. Flow Control".
"Continu-Flo Administration Set", (p. 2).
National Intravenous Therapy Association, (vol. 4).

Primary Examiner—Dalton L. Truluck
Attorney, Agent, or Firm—Richards, Harris & Medlock

[57] ABSTRACT

An improved fluid additive system is disclosed. The first embodiment of the invention is formed by a system (10) including a controller (26) which automatically delivers a preselected quantity of a secondary fluid from a secondary container (14) at a preselected rate and subsequently delivers a preselected quantity of a primary fluid from a primary container (12) at a preselected rate. Within the controller (26) are input controls (48) for operator input of the desired preselected rates and quantity of fluid to be infused. A passive metering unit (36, 36') is provided in the controller for metering a known quantity of fluid to a delivery line upon each activation thereof. A microprocessor (40) responds to the rates amd quantity input into the input controls (48) to direct a drive unit (38) to activate the metering unit (36) to achieve the desired rates and quantity of infusion of the primary and secondary fluids.

21 Claims, 4 Drawing Figures

INTRAVENOUS DRUG ADDITIVE DELIVERY SYSTEM WITH ELECTRONIC CONTROL

TECHNICAL FIELD

This invention relates to patient care, in particular this invention relates to intravenous drug addition.

BACKGROUND ART

Intravenous drug additive systems have been used in patient care for many years. These systems typically operate by gravity induced flow from a container into the patient.

Quite often it is desirable to add more than one fluid intravenously to the patient. While two or more separate venous entries may be made, each entry increases the risk of infection and other harmful results. Therefore, it has been recognized as desirable to employ a drug additive system in which a primary fluid is added intravenously with a secondary fluid being added intermittently through the same entry ("piggy backing") The primary fluid may function as fluid replacement, keep vein open (KVO) fluid, nutritional fluids, blood or other drugs. The secondary fluid may commonly be antibiotics, anticoagulants, antihypertensives, cardiovascular agents or other medicaments.

Traditionally, both primary and secondary fluids have been stored in glass bottles or flexible plastic bags suspended above the patient. A drip chamber is either to or integral with the bottle or bag. An orifice of predetermined diameter interconnects the drip chamber with the fluid in the container. A flexible tube extends from the container to the patient. An early form of single fluid delivery system employing gravity, still widely used, incorporates the drip chamber and a manually set pinching device. A nurse or aide may visually count the drop rate in the chamber and manually set the pinching device on the delivery tubing to achieve a desired flow rate. Fluid delivery systems of this type are not highly accurate. The volume of each drop of fluid dripping into the drip chamber may not be uniform. The drop size is dependent on the orifice diameter, which may vary within a manufacturing tolerance for a particular intravenous giving set manufactured. In addition, even the nominal orifice diameter is not uniform throughout the industry. Manufactures sell drip chambers having 10, 15, 20 and 60 drops/milliliter, for example. Confusion and improper application can result. The volume of the fluid drops may also vary with temperature and viscosity.

The gravitational head pressure which acts to infuse the fluid into the patient may vary. In addition, the tubing cooperating with the pinching device may relax, varying the restriction of flow and permitting inaccuracy in delivery to the patient.

All of these problems require the nurse or aid to be continuously vigilant of the flow rate and permit error.

Drop counting has been used for many years as the standard technique for flow control in IV applications because of its relative simplicity. However, the goal in infusion is to accurately determine the volume of fluid infused.

Although such systems suffer from the inaccuracies noted above and require special attention from nursing personnel, they have formed the basis for additive or "piggyback" systems to introduce a secondary fluid. Such arrangements are described for example in a brochure entitled "New Concepts in Intermittent IV Therapy", published by Travenol Laboratories Inc., Deerfield, Ill. In a typical prior art set up, the secondary fluid or medicament container is elevated above the level of the primary fluid container. A check valve is placed in the line extending from the primary container and the lines from both containers are connected through a Y-connector to a single delivery line for delivery to a patient. The gravitational head of the secondary fluid in the secondary container closes the check valve to prevent flow from the primary container. The system will deliver the secondary fluid to the patient and thereupon automatically commence delivery of the primary fluid as the check valve opens. The delivery of both fluids, however, is made with the same inaccuracies noted above inherent in this type of system. Moreover, the large number of manipulations necessary by the nurse or aide in the operation of this system gives rise to the potential for error. Unless adjustment is made by the nurse after the secondary fluid delivery is complete, both fluid deliveries operate through the same pinch setting.

One technique for improving on the accuracy of intravenous delivery has been the use of positive pressure volumetric pumps which force fluid into the patient. One such pump is sold as the LifeCare IV pump system manufactured by Abbott Laboratories, Hospital Products Division, North Chicago, Ill. 60064. While positive pressure volumetric pumps improve the accuracy of delivery of the fluid compared to the prior described system, several disadvantages exist.

The positive pressure generated by the pump increases the dangers from potential infiltration of the fluid into the tissues of the patient which can result from improper catheter placement. When employed with a "piggyback" delivery system with the pump downstream of the Y-connector, the pump will draw both primary and secondary fluids from both containers until the secondary container, which commonly has a smaller capacity than the primary container, is empty. Therefore, the secondary fluid is diluted with the primary fluid at an unknown rate. In addition, the known pumps typically provide only a single flow rate once the pump is set.

One improvement in the use of positive volumetric pressure pumps has been to manually clamp the primary fluid delivery line to insure the infusion of the secondary fluid at full strength. However, this requires the nurse to return to bedside to manipulate the clamp after the secondary infusion is complete, and monitor the flow to begin the primary fluid infusion. In addition, the potentially serious problems from infiltration remain. A pump may be positioned in the secondary delivery line of the system to deliver the secondary fluid under positive pressure. However, the nurse must also return to the bedside after the secondary fluid is exhausted and the danger of infiltration remains a concern.

Drop counting controllers which include drop sensors for monitoring the drip rate in a drip chamber and controlling a tube pinch device have been employed with a piggyback system. One such controller is manufactured by Imed Corporation of 9925 Carroll Canyon Road, San Diego, Calif. as model 350.

The drop counting controllers have several disadvantages. The drop sensors must rely on the accuracy of drop volume. The drop counting controller operates by sensing the passage of a drop past an optical or other sensor and computing the flow rate based on an assumed drop volume. The drip volume in actuality may differ, based on differing orifice diameters, viscosity or other causes noted above.

The typical drop counting controller includes only a single drop sensor. Therefore, the nurse or aide must position the drop sensor on the drip chamber of the secondary container to control the rate of infusion of the secondary fluid. The nurse or aide must monitor the flow of the secondary fluid to determine when the secondary fluid has been infused and subsequently move the drop sensor to the drip chamber of the primary container to control the rate of infusion of the primary fluid.

It has been suggested to improve the system by employing two drop counting controllers, each having drop sensors. One drop counting controller will have its drop sensor positioned at the drip chamber of the secondary container and will infuse the secondary fluid until the secondary container is empty. This controller then signals the other controller having its drop sensor at the drip chamber of the primary container to initiate infusion of the primary fluid. However, this system is also subject to the inaccuracies of the drip chamber. It is also expensive in duplicating elements of sensors and electronic sets.

SUMMARY OF THE INVENTION

In accordance with the present invention, an apparatus for intravenous addition of a primary and secondary fluid to a patient is provided. The apparatus includes a primary container for holding the primary fluid and a secondary container for holding the secondary fluid, the fluid in the secondary container being elevated above the fluid in the primary container. Primary and secondary fluid delivery lines extend from the primary and secondary containers, respectively. A connector is provided for combining the flow from the primary and secondary fluid delivery lines. A check valve is provided for preventing flow from the secondary container to the primary container. Finally, a controller is provided. The connector directs the fluid flowing from the primary and secondary fluid delivery lines into the controller and the controller permits flow therethrough at a first flow rate representing the desired flow rate of the secondary fluid. The controller further senses the discharge of a predetermined volume of the secondary fluid and subsequently permits flow therethrough at a second flow rate representing the desired flow rate of the primary fluid.

In accordance with yet another aspect of the present invention, still another apparatus for intravenous addition of a primary and secondary fluid to a patient is provided. The apparatus includes a primary container for holding the primary fluid and a secondary container for holding the secondary fluid positioned above the primary container. A controller is provided for variable control of the flow rate of fluid therethrough, the controller further measuring the total flow therethrough from an initial setting. Primary and secondary fluid delivery lines extend from the primary and secondary containers, respectively. A connector combines the flow from the primary and secondary fluid delivery lines for entry into the controller. A check valve is positioned in the primary fluid delivery line to prevent secondary fluid from entering the primary container. A delivery line extends from the controller to the patient for flow of metered fluid therethrough. The controller delivers a predetermined quantity of fluid at a predetermined rate to deliver the seconday fluid, the controller sensing the flow of the predetermined quantity of fluid therethrough and subsequently delivering fluid at a second predetermined rate to deliver the primary fluid.

In accordance with yet another aspect of the present invention, the controller includes a metering unit. The metering unit includes first and second halves adapted to be secured in facing relation. Each of the halves is constructed to form a reservoir portion, entry and exit channels extending from the reservoir portion and entry and exit port sections. The entry and exit channels and entry and exit port sections are interconnected by entry and exit orifices, respectively. The reservoir portions form a reservoir and the entry and exit port sections form entry and exit ports, respectively, when the halves are secured in facing relation. A flexible diaphragm structure is positionable between the halves to divide the reservoir into first and second compartments. First entry valve means and first exit valve means are attached to the first half. Each of the first entry and exit valve means is movable from an open position permitting flow through the entry and exit orifices, respectively to a closed position to prevent flow therethrough. Second entry valve means and second exit valve means are attached to the second half. The second entry and exit valve means are each movable from an opened position permitting fluid flow through the entry and exit orifices in the second half, respectively, to a closed position preventing flow therethrough. Activating structure is provided for alternately opening and closing each of the valves. The first entry valve structure and second exit valve structure are opened and closed simultaneously. The second entry valve structure and first exit valve structure are also opened and closed simultaneously and opposite the first entry valve structure and second exit valve structure. Fluid entering the entry port from the connector through the entry orifice and entry channel of the first half to the first compartment when the first entry valve structure is opened. The fluid entering the entry port has a sufficient pressure head to move the diaphragm structure to force the fluid in the second compartment through the exit channel and exit orifice of the second half and into the delivery line. Fluid entering the entry port from the connector flows through the entry orifice and entry channel of the second half into the second compartment when the second entry valve structure is open. The fluid entering the entry port has sufficient pressure head to move the diaphragm structure to force the fluid in the first compartment through the exit channel and exit orifice of the first half and into the delivery line. The volume of the fluid displaced from each of the first and second compartments is predetermined.

BRIEF DESCRIPTION OF THE DRAWINGS

A more complete understanding of the invention and its advantages will be apparent from the following Detailed Description when taken in conjunction with the accompanying Drawings, in which.

DETAILED DESCRIPTION

Figure 1:
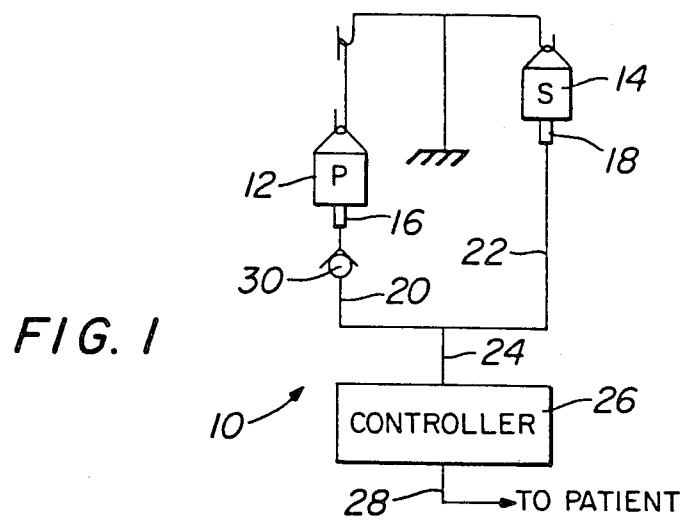
FIG. 1 illustrates a first embodiment of the present invention incorporating a controller determining the flow rate and accumulated flow from both primary and secondary containers.

Referring now to the Drawings, wherein like reference characters designate like or corresponding parts throughout several views, the preferred embodiment of the present invention is a drug additive system 10 which is illustrated in FIG. 1 and described hereinbelow. Several advantages are provided by this system. The system 10 is fully programmable for accurate measurement of flow rate and total flow for both the secondary and primary fluids. The secondary fluid will be infused at full strength. The system utilizes gravity alone as the driving force for infusion, thereby increasing reliability. The preferred embodiment does not incorporate drop sensors, thereby eliminating the error inherent in drip chamber flow and complexity in the system.

The system 10 forming the first embodiment of the present invention includes primary container 12 and secondary container 14 for containing the primary and secondary fluids, respectively. The containers may be constructed of flexible plastic or glass bottles. Each of the containers is illustrated having a drip chamber 16 and 18, respectively. However, the drip chambers are not necessary for the operation of this embodiment. The secondary container 14 is suspended above the primary container so that the secondary fluid within the secondary container is elevated above the primary fluid in the primary container. Therefore, the gravity potential or pressure head of the secondary fluid is greater than the primary fluid.

A primary fluid delivery line 20 extends downwardly from the primary container. A secondary fluid delivery line 22 extends downwardly from the second container 14. The primary and secondary fluid delivery lines are fed into a connector 24 forming a Y connection. Any fluid flowing through the primary and secondary fluid delivery lines is combined in the connector which extends to the input of a controller 26. A delivery line 28 extends from the output of controller 26 to the patient. A check valve 30 is positioned in the primary fluid delivery line 20 to prevent flow from the secondary container into the primary container.

Figure 2:
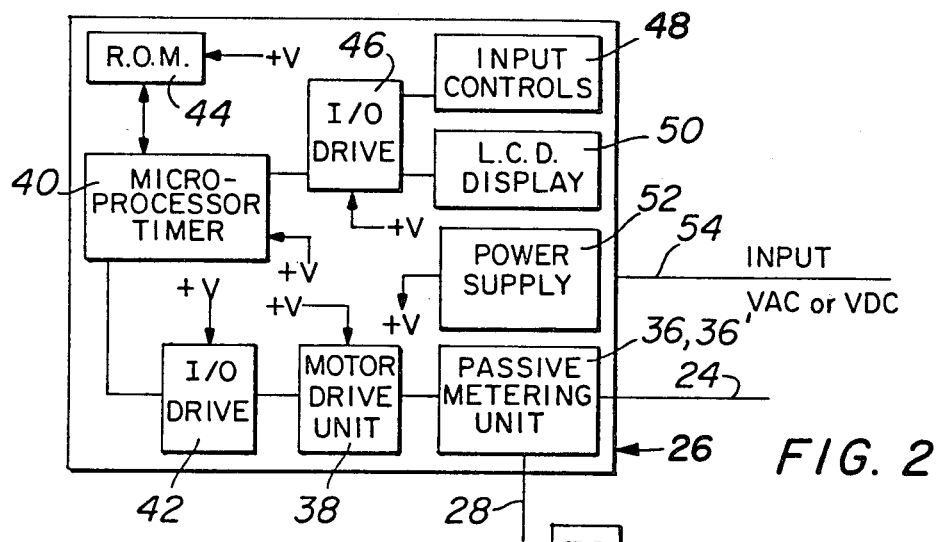
FIG. 2 illustrates in greater detail the construction of the controller employed in the first embodiment of the present invention.

The details of controller 26 are better illustrated with reference to FIG. 2. The controller 26 includes a passive metering unit 36 which meters a known quantity of fluid therethrough. The preferred embodiment of the passive metering unit is the unit 36' illustrated in FIG. 4 and described hereinafter. The passive metering unit may also be one as described and claimed in copending application Ser. No. 071,843, filed Sept. 4, 1979 and assigned to the Assignee of the present invention which disclosure is herein incorporated by reference.

Figure 3:
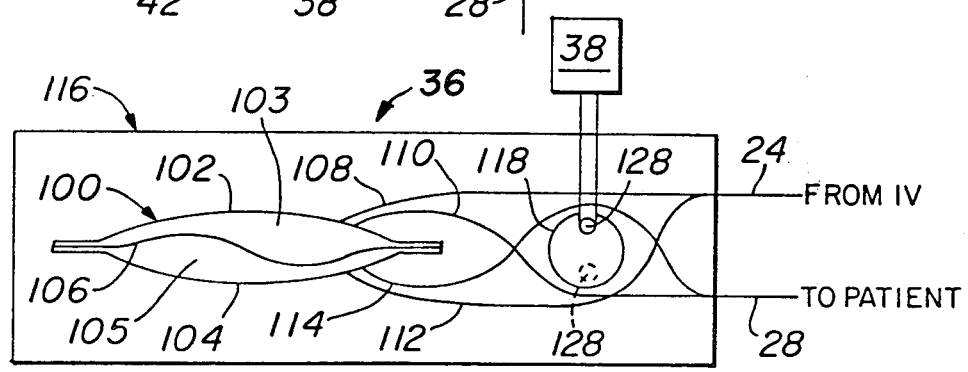
FIG. 3 illustrates a passive metering unit for use in the present invention.

The detail of one passive metering unit disclosed in the copending application Ser. No. 071,843 is illustrated in FIG. 3 and described below. The passive metering unit 36 includes a dual compartment metering chamber 100 within block 116. The metering chamber 100 is defined by a pair of complimentary chamber walls 102 and 104. The chamber walls 102 and 104 are each formed of similar, relatively rigid and inflexible biologically inert material, such as teflon or polyvinyl chloride or similar plastics, or may alternatively be formed of a flexible material, such as a silicone elastomer if mounted so that they are inelastic. Each of the chamber walls 102 and 104 is formed as an identical complimentary hemispherical depression in a sheet of the material. The two sheets of material into which the chamber walls 102 and 104 are formed are joined together and pressed between them is a movable pressure transmitting member 106. The pressure transmitting member 106 is formed as a membrane of relatively flexible material, such as silicone elastomer or a thin teflon sheet which is pressed between the sheets of material in the chamber walls 104 and 102. The pressure transmitting member 106 is held between the sheets of material of the chamber walls 102 and 104 in such a fashion that the portion of the pressure transmitting member 106 inside of the chamber 100 is not stretched taut, but instead remains in a relatively limp, flexible condition. A first compartment 103 is defined between the chamber wall 102 and the pressure transmitting member 106 and a second compartment 105 is defined between the compartment wall 104 and the pressure transmitting member 106. The compartments 103 and 105 are completely sealed from each other by the pressure transmitting member 106. A first inlet tube 108 and a first outlet tube 110 are connected through the chamber wall 102 to the interior of the first compartment 103. Similarly, a second inlet tube 112 and a second outlet tube 114 are connected through the chamber wall 104 into the interior of the second compartment 105.

The first inlet tube 108 and second outlet tube 114 pass a hole 118 on a first side. The first outlet tube 110 and second inlet tube 112 pass on the other side of hole 118. On the far side of hole 118, inlet tubes 108 and 112 are joined to form connector 24. The outlet tubes 110 and 114 are joined to form delivery line 28.

A rod 128 is movable between first and second positions by the drive unit 38. In the first position, illustrated in FIG. 3 in solid line, the tubes 108 and 114 are pressed closed while the tubes 110 and 112 are open. In the second position shown in phantom line, the rod 128 closes tubes 110 and 112 while tubes 108 and 114 are open.

When rod 128 is in the first position, fluid in connector 24 is forced under pressure into second compartment 105 as a result of the pressure head. As the second compartment 105 fills with fluid, the pressure transmitting member 106 is slowly pressed upward, thereby pressing fluid out of the first compartment 103, through first outlet tube 110 for infusion into the patient. When the pressure transmitting member 106 is pressed against the interior of the chamber wall 12, no additional fluid can pass into the chamber through the second inlet tube 112 and fluid flow stops. This condition persists until the rod 128 moves to the second position. When this occurs, the first inlet tube 108 admits fluid under pressure into the first compartment 103. As fluid fills the first compartment 103, the flexible pressure member 106 is forced downwardly thereby displacing fluid from the second compartment 105 through the second outlet tube 114 for infusion to the patient. This flow continues until the pressure transmitting member 106 is pressed against the chamber wall 104 of the metering chamber 100, at which time fluid flow ceases.

It can be readily perceived that the two stages of operation of the device result in the transmission of identical volumes of fluid to the patient. The amount of fluid metered is determined by the volume of the compartments. The pressure head of the fluid within connector 24 is immaterial provided it is sufficient to move the member 106. Therefore, movement of the patient, changing the pressure head of the fluid relative to the patient, does not affect operation of the metering unit.

The volume of fluid infused in the patient may be exactly controlled by the metering unit 36 by controlling the timing of the activation of the rod 128 into the first and second positions. This function is performed by the motor drive unit 38 in cooperation with the microprocessor 40.

Figure 4:
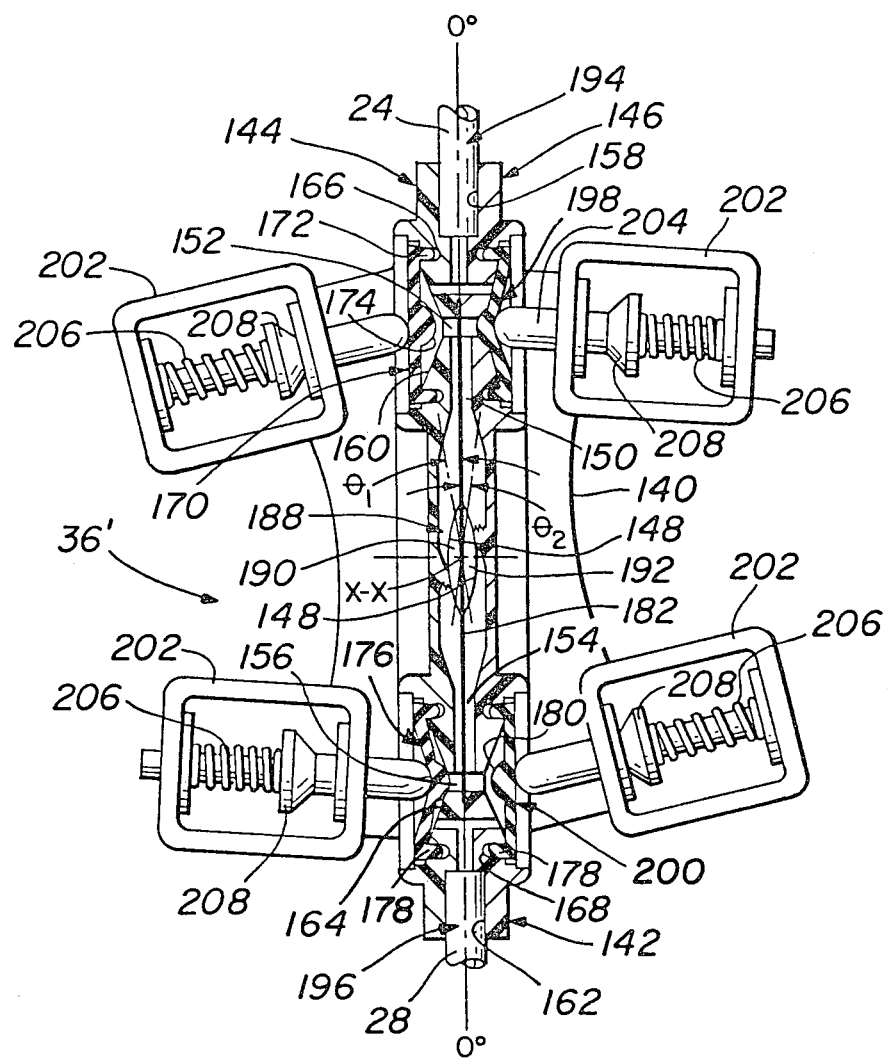
FIG. 4 illustrates a preferred metering unit for use in the present invention.

The detail of the preferred construction of the metering unit is illustrated in FIG. 4 and described below. The preferred metering unit is identified as 36'. It will be understood that metering unit 36' may be substituted for metering unit 36.

Metering unit 36' includes a frame 140 and a cassette 142 secured to a member (not shown). The cassette 142 comprises two halves 144 and 146. Each half is identical and includes a hemispherical reservoir portion 148. An entry channel 150 is formed which extends from portion 148 to an entry orifice 152. An exit channel 154 is formed which extends from the portion 148 to an exit orifice 156. The volume of channels 150 and 154 is substantially less than the volume of portion 148.

An entry port portion 158 is formed at the end of each half near entry orifice 152. The entry port portion 158 has one end opening through a seal surface 160 surrounding the entry orifice 152.

A similar exit port portion 162 is formed in each half near the exit orifice 156. One end of the exit port portion extends through a seal surface 164 surrounding the orifice 156.

Annular notches 166 and 168 are formed in each half and are concentric with the entry and exit orifices 152 and 156, respectively. An entry valve 170 formed of an elastomeric material is provided with a lip 172 for sealing enagement within the annular groove 166 on half 144. The entry valve 170 includes a hemispherical sealing face 174 which may be moved into sealing engagement with the seal surface 160. An exit valve 176 is provided with lips 178 for sealing engagement in the annular groove 168 on half 144. The exit valve includes a hemispherical sealing face 180 for sealing engagement with the seal surface 164. An identical entry valve 198 and exit valve 200 are provided for half 146.

The two halves 144 and 146 are designed to be secured in a facing relation and separated by a flexible diaphragm 182. The halves may be maintained in this relation by any common means, such as threaded screws, rivets, bolts, etc.

When the halves 144 and 146 are in the facing relation to form cassette 142 as shown in FIG. 4, the hemispherical reservoir portions combine to form a spherical reservoir 188 separated into a first compartment 190 and a second compartment 192 by the flexible diaphragm 182. The flexible diaphragm 182 also prevents fluid flow between the channels within either half. The entry port portions 158 of each half combine to form an entry port 194 connected to connector 24. The exit port portions 162 of the two halves combine to form an exit port 196 connected to delivery line 28.

When the entry valve 170 and exit valve 176 on half 144 and entry valve 198 and exit valve 200 on half 146 are in the open position, fluid flow is permitted through the associated ports. Valves 170 and 200 are open in FIG. 4. When the valves are deflected inward in the half to which they are secured, the valve will close and prevent fluid flow through the associated port.

Valve 176 and valve 198 are shown in the closed position in FIG. 4.

The frame 140 is pivotable relative to cassette 142 about an axis X-X centered through the reservoir 188. The range of motion extends to angles $\theta_1$ and $\theta_2$ on either side of zero deflection. The frame 140 is shown in FIG. 4 pivoted to angle $\theta_1$. Members 202 are positioned at the four corners of frame 140 for guiding rods 204. The rods 204 are urged toward the cassette by springs 206 acting between members 202 and collars 208 on each of the rods. The tip of each of the rods lies adjacent a valve in cassette 142.

When frame 140 is centered with respect to the cassette 142 at zero deflection, the springs 206 urge the rods 204 into engagement with the associated valves to close the valves and prevent fluid flow through the cassette. The metering unit may be activated if the frame 140 is pivoted clockwise or the cassette 142 counterclockwise to the $\theta_1$ position shown in FIG. 4. It will be seen that the rods acting on exit valve 200 and entry valve 170 have been withdrawn to permit the valves to move to the open position. The entry valve 198 and exit valve 176 are retained in the closed position. Activation of the metering unit to open and close the alternate pairs of valves will permit the metering of the predetermined volume of fluid into the exit port 196 and delivery line 28 for infusion into the patient upon each activation thereof.

In operation, the metering unit 36' may be activated by pivoting frame 140 to the $\theta_2$ position where the entry valve 198 and exit valve 176 will be open. This will permit fluid to flow from the connector 24 at the higher pressure head through the entry port 194 and into the second compartment 192. As the fluid flows into the second compartment 192, it deflects the flexible diaphragm 182 toward the inner surface of the reservoir portion 148 of half 144 until the second compartment has a volume substantially equal to the entire reservoir 188 and the first compartment 190 has substantially zero volume. Were fluid present in the first compartment 190, the fluid would be at a lower pressure head than the fluid in the second compartment 192 with the entry valve 170 in the closed position. The fluid entering the second compartment would urge the fluid in the first compartment through the open exit valve 176 and to the exit port 196 for infusion into the patient.

The metering unit is subsequently activated by pivoting frame 140 to the $\theta_1$ position where the entry valve 170 and exit valve 200 are opened. Simultaneously, the exit valve 176 and entry valve 198 are again moved to the closed position. Fluid from the connector 24 then flows through the entry port 194 and into the first chamber 190. The relatively higher pressure head of the fluid entering the first compartment urges the flexible diaphragm 182 toward the inner surface of the reservoir portion of half 146, forcing the fluid in the second compartment past the exit valve 200 and into the exit port 196 for infusion into the patient.

It is clear that the alternate opening and closing of the pairs of valves formed by entry valve 170 and exit valve 200 forming the first pair and exit valve 176 and entry valve 198 forming the second pair upon each activation of the metering unit permits a predetermined quantity of fluid having a volume substantially equal to the volume of the reservoir 188 to be metered into the exit port 196 for infusion. In the preferred embodiment, the volume of the reservoir 188 is approximately 0.1 cc. Therefore, upon each activation of the metering unit, 0.1 cc of fluid is delivered for infusion into the patient.

Motor drive unit 38 may be used to activate metering unit 36' by pivoting the frame 140 between the $\theta_1$ and $\theta_2$ positions. When not activated, frame 140 will be maintained in the zero deflection position.

Drive unit 38 is preferably operable within a range of speeds to vary the rate of activation of metering units 36 and 36' to permit setting of the flow rate through the passive metering unit. A substantial advantage of the drive unit and passive metering unit combination is the fact that gravity is used as the driving force of the fluid passing through the metering unit.

The drive unit 38 is controlled by a microprocessor 40 through an input/output drive 42. Microprocessor 40 may comprise a Model 6805 manufactured by Motorola, Inc., Semiconductor Group, 5005 E. McDowell Rd., Phoenix, Arizona. However, any other suitable device may be employed to perform the function of microprocessor 40. It is obvious to one trained in the art that the function of microprocessor 40 may be duplicated by hard-wired electronics. Therefore it should be understood that it is within the scope of the present invention to substitute such an electronic control without departing from the scope and spirit of the invention. A microprocessor based control device is preferred, however. A read only memory (ROM) 44 is interconnected with the microprocessor 40. A second input/output drive 46 interconnects the microprocessor with operator input controls 48 and liquid crystal display (L.C.D.) 50.

The operator will input to input controls 48 the desired infusion rate and total infusion volume desired for both the primary and secondary fluids. The input will be translated to machine language in I/O drive 46 and entered into microprocessor 40. The desired rate of infusion for both fluids and the instantaneous volume of each fluid infused will be processed from microprocessor 40 through I/O drive 46 and displayed on the liquid crystal display 50 for viewing by the operator.

The main program for operation of controller 26 will be contained in the ROM 44. This includes all the algorithms necessary to drive the liquid crystal display 50 and determine the speed of drive unit 38 necessary to achieve the desired flow rate. The ROM 44 may comprise a Model 5354 manufactured by Intersil of 10710 North Tantau Avenue, Cupertino, California. This ROM is an electrically programmable and erasable model. The memory may only be erased by exposure to ultraviolet light. However, any other suitable device may be employed to perform the function of ROM 44.

In response to the input commands from the operator, the microprocessor transmits through I/O drive 42 to drive unit 38 the necessary commands to permit the secondary fluid fluid to flow through the controller at the determined rate until the determined volume of fluid passes therethrough. The secondary container will contain the desired quantity of secondary fluid to be delivered so that when the controller resets the flow rate therethrough to the predetermined rate for the primary fluid, the check valve 30 will open to initiate flow of the primary fluid. The microprocessor 40 will typically include a timing device which may be used to set the proper operating speed for the drive unit 38 to achieve the predetermined infusion rate. The timing device will also include an accumulator for real time measurement of the volume of fluid infused. The controller 26 may also include a bubble detector for detecting bubbles within the system 10 to prevent embolism.

The advantages of the present system are readily apparent from the discussion above. System 10 provides monitor-free infusion of a predetermined quantity of secondary fluid at a predetermined rate. When the predetermined quantity of the secondary fluid is infused, the systems automatically begin infusion of the primary fluid at a second preselected rate. The use of a passive metering unit increases the reliability of the system as it depends on gravity alone and prevents overpressure of the fluid being infused.

Although only one embodiment of the present invention has been illustrated in the accompanying drawings and described in the foregoing Detailed Description, it will be understood that the invention is not limited to the embodiment disclosed, but is capable of numerous rearrangements, modifications and substitutions of parts and elements without departing from the scope and spirit of the invention.

I claim:

1. An apparatus for intravenous addition of a primary and secondary fluid to a patient comprising:
   a primary container for holding the primary fluid;
   a secondary container for holding the secondary fluid, the fluid in said secondary container being elevated above the fluid in said primary container;
   primary and secondary fluid delivery lines extending from said primary and secondary containers, respectively;
   a connector for combining the flow from said primary and secondary fluid delivery lines;
   check valve means for permitting the secondary fluid to flow through the connector until the secondary container is empty and subsequently permitting the primary fluid to flow through the connector; controller means for controlling fluid flow to the patient, said connector directing the fluid flowing therethrough from said primary and secondary delivery lines into said controller means, said controller means including:
   metering means for initially metering flow therethrough to the patient at a preselected flow rate representing the desired infusion rate of the secondary fluid;
   sensing means for sensing the passage of a predetermined quantity of fluid equal to the quantity of secondary fluid which is to be infused;
   said metering means subsequently metering flow therethrough at a second preselected flow rate representing the desired infusion rate of the primary fluid to the patient; and
   a combined fluid delivery line extending from said controller means to the patient for transferring the fluid metered through said controller means to the patient for infusion.

2. The apparatus of claim 1 wherein said controller means further includes:
   input means for input by an operator of preselected flow rates representing the desired flow rates of the primary and secondary fluids and the preselected quantity of secondary fluid representing the desired quantity of secondary fluid infused in the patient;
   said metering means permitting fluid flow within a range of flow rates; and
   microprocessor means communicating with said input means and said metering means, said microprocessor means activating said metering means to meter fluid at a rate corresponding to the preselected flow rate for the secondary fluid input to said input means until a quantity of fluid has been metered therethrough corresponding to the preselected quantity of secondary fluid, said microprocessor means thereafter activating said metering means to meter fluid at the rate corresponding to the preselected rate for the primary fluid input to said input means.

3. The apparatus of claim 1 wherein said metering means comprises:
one chamber for holding a predetermined volume of fluid, said chamber being divided into first and second compartments by a flexible diaphragm;
inlet tubes extending from said connector to each of said compartments for filling said compartments with fluid from said connector;
outlet tubes extending from said compartments for permitting flow therethrough to the patient;
valve means for selectively opening and closing said inlet and outlet tubes connected to each of said compartments such that fluid flow is allowed alternately in said inlet and outlet tubes;
said controller means including microprocessor means for alternately activating said valve means between first and second positions, said valve means permitting a predetermined volume of fluid to flow into said second compartment and permitting a predetermined volume of fluid to flow from said first compartment through one of said outlet tubes in the first position, said valve means permitting a predetermined volume of fluid to flow into said first compartment and permitting a predetermined volume of fluid to flow from said second compartment through the other of said outlet tubes in said second position, said controller means controlling the frequency of activation to determine the fluid flow rate to the patient and accumulating the quantity of activations to determine the quantity of fluid delivered to the patient.

4. The apparatus of claim 2 wherein said metering means comprises:
first and second halves adapted to be secured in facing relation, each of said halves being constructed to form a reservoir portion, entry and exit channels extending from the reservoir portion and entry and exit port sections, the entry and exit channels and entry and exit port sections being interconnected by entry and exit orifices, respectively, the reservoir portions of each half forming a reservoir and said entry and exit port sections forming entry and exit ports, respectively, when said halves are secured in facing relation, the entry port being connected to said connector and said exit port permitting flow therethrough to the patient;
a flexible diaphragm means for positioning between said first and second halves when secured in facing relation to divide the reservoir into first and second compartments;
first entry valve means and first exit valve means for attachment to said first half, each of said first entry and exit valve means being movable from an open position permitting fluid flow through the entry and exit orifices, respectively, to a closed position to prevent flow through the entry and exit orifices, respectively;
second entry valve means and second exit valve means for attachment to said second half, each of said second entry and exit valve means being movable from an open position permitting fluid flow through the entry and exit orifices, respectively, to a closed position to prevent fluid flow through the entry and exit orifices, respectively; and
activating means for alternately opening and closing each of said valves, said activating means being activated by said microprocessor means, said first entry valve means and said second exit valve means simultaneously being opened and closed and said second entry valve means and said first exit valve means being simultaneously opened and closed to positions opposite said first entry valve means and said second exit valve means;
whereby fluid entering said entry port flows through the entry orifice and entry channel of said first half into the first compartment when said first entry valve means is open, the fluid entering said entry port having sufficient pressure head to move said diaphragm means to force the fluid in the second compartment through the exit channel and exit orifice of said second half to the exit port, and fluid entering said entry port flows through the entry orifice and entry channel of said second half into the second compartment when said second entry valve means is open, fluid entering said entry port having sufficient pressure head to move said diaphragm means to force the fluid in the first compartment through the exit channel and exit orifice of said first half to the exit port, the fluid displaced from each of the first and second compartments having a predetermined volume.

5. The apparatus of claim 2 wherein said microprocessor means further includes timer means for determining the quantity of fluid metered at the rate corresponding to the preselected rate for the secondary fluid, said microprocessor means activating said metering means to meter fluid at the rate corresponding to the preselected rate for the primary fluid when said timing means measures a quantity corresponding to the preselected quantity of secondary fluid.

6. An apparatus for intravenous infusion of a primary and secondary fluid to a patient comprising:
a primary container for holding the primary fluid;
a secondary container for holding the secondary fluid, said secondary container being positioned so that the secondary fluid in said secondary container is positioned above the primary fluid in said primary container;
a controller;
a primary fluid delivery line extending from said primary container;
a secondary fluid delivery line extending from said secondary container;
a connector combining fluid flowing through said primary and secondary fluid delivery lines, said connector extending into said controller;
a check valve positioned in said primary fluid delivery line permitting the secondary fluid to flow from the secondary container through the connector until the secondary container is empty and subsequently permitting the primary fluid to flow from the primary container through the connector;
a delivery line extending from said controller to the patient for infusion of fluid flowing therethrough; and
said controller initially permitting fluid to flow therethrough from said connector to said delivery line for infusion into the patient at a rate corresponding to a preselected rate of infusion of the secondary fluid, said controller further sensing the passage therethrough of a quantity of fluid corresponding to a preselected quantity of secondary fluid to be infused and subsequently permitting fluid to flow therethrough at a rate corresponding to a preselected rate of infusion of the primary fluid.

7. The apparatus of claim 6 wherein said controller includes:

an input control for input by an operator of the preselected rate of infusion of the primary and secondary fluids and the preselected quantity of secondary fluid to be infused;

a metering unit for metering fluid from said connector to said delivery line, a known quantity of fluid being metered into said delivery line upon each activation of said metering unit;

a drive unit for activating said metering unit, said drive unit permitting a variable rate of activation of said metering unit to vary the rate of flow of fluid through said controller; and microprocessor means communicating with said input control and said drive unit, said microprocessor means directing said drive unit to activate said metering unit to meter fluid flow at a rate corresponding to the preselected rate of infusion of the secondary fluid until a fluid quantity equal to the preselected quantity of secondary fluid has been infused in the patient, said microprocessor means thereafter directing said drive unit to meter fluid flow at a rate corresponding to the preselected rate fro the primary fluid.

8. The apparatus of claim 7 wherein said metering unit comprises:

a metering chamber having first and second compartments formed therein;

first and second inlet tubes connected respectively to the first and second compartments;

first and second outlet tubes connected respectively to the first and second compartments;

valve means activatable for selectively opening and closing each of said inlet and outlet tubes such that fluid flow is allowed alternately in both said first inlet tube and said second inlet tube and in both said second inlet tube and said first outlet tube, said inlet tubes being connected to said connector and said outlet tubes being connected to said delivery line; and a movable pressure transmitting member positioned between said first and second compartments in said metering chamber, said pressure transmitting member forming a movable portion of each of said compartments and being movable between two positions such that the two compartments are simultaneously and alternately filled and emptied, the movement of said pressure transmitting member displacing a predetermined and equal amount of fluid in moving between the two positions so that the amount of fluid alternately displaced from each of the two compartments is equal, said drive unit activating said valve means to permit fluid flow through one of said inlet tubes into the associated compartment to act against said pressure transmitting member to urge the fluid in the alternate compartment through the associated outlet tube for delivery to the patient, said microprocessor means controlling the rate of activation to determine the flow rate and accumulating the number of activations to determine the quantity of fluid metered through said metering unit to the patient.

9. The apparatus of claim 7 wherein said metering unit comprises:

first and second halves adapted to be secured in facing relation, each of said halves being constructed to form a reservoir portion, entry and exit channels extending from the reservoir portion and entry and exit port sections, the entry and exit channels and entry and exit port sections being interconnected by entry and exit orifices, respectively, the reservoir portions of each half forming a reservoir and said entry and exit port sections forming entry and exit ports, respectively, when said halves are secured in facing relation, the entry port being connected to said connector and the exit port being connected to said delivery line;

a flexible diaphragm means for positioning between said first and second halves when secured in facing relation to divide the reservoir into first and second compartments;

first entry valve means and first exit valve means for attachment to said first half, each of said first entry and exit valve means being movable from an open position permitting fluid flow through the entry and exit orifices, respectively, to a closed position to prevent flow through the entry and exit orifices, respectively;

second entry valve means and second exit valve means for attachment to said second half, each of said second entry and exit valve means being movable from an opening position permitting fluid flow through the entry and exit orifices, respectively, to a closed position to prevent fluid flow through the entry and exit orifices, respectively; and activating means for alternately opening and closing each of said valves, said drive unit activating said metering unit by directing said activating means to change the position of each of said valves, said first entry valve means and said second exit valve means simultaneously being opened and closed and said second entry valve means and said first exit valve means being simultaneously opened and closed to positions opposite said first entry valve means and said second exit valve means;

whereby fluid entering said entry port flows through the entry orifice and entry channel of said first half into the first compartment when said first entry valve means is open, the fluid entering said entry port having sufficient pressure head to move said diaphragm means to force the fluid in the second compartment through the exit channel and exit orifice of said second half to the exit port, and fluid entering said entry port flows through the entry orifice and entry channel of said second half into the second compartment when said second entry valve means is open, fluid entering said entry port having sufficient pressure head to move said diaphragm means to force the fluid in the first compartment through the exit channel and exit orifice of said first half to the exit port, the fluid displaced from each of the first and second compartments having a predetermined volume.

10. The controller of claim 7 wherein said microprocessor means includes timing means for accumulating the number of activations of said metering unit by said drive unit to determine the quantity of fluid metered to said delivery line, said microprocessor means directing said drive unit to activate said metering unit to meter fluid at a rate corresponding to the preselected rate for the primary fluid when said timing means measures a quantity of fluid flowing through said controller corresponding to the preselected quantity of secondary fluid to be infused in the patient.

11. An apparatus for intravenous infusion of a primary and secondary fluid into a patient, comprising:
a primary container for holding the primary fluid;
a secondary container for holding the secondary fluid, said secondary container being positioned so that the secondary fluid contained therein is positioned above the primary fluid in said primary container;
a controller positioned below said primary and secondary containers;
a primary fluid delivery line extending from said primary container;
a secondary fluid delivery line extending from said secondary container;
a connector combining the fluid flow in said primary and secondary fluid delivery lines and delivering the fluid to said controller;
a check valve positioned in said primary fluid delivery line permitting the secondary fluid to flow from the secondary container through the connector until the secondary container is empty and subsequently permitting the primary fluid to flow from the primary container through the connector;
a delivery line extending from said controller to the patient for infusion of the fluid flowing therethrough; and
said controller including:
(a) a metering unit for metering a known quantity of fluid into said delivery line upon each activation thereof,
(b) a drive unit for activating said metering unit,
(c) input controls for operator input of the preselected rate and quantity of primary and secondary fluids to be infused into the patient, and
(d) microprocessor means for directing said drive unit to activate said metering unit to meter fluid into said delivery line at a rate corresponding to the preselected rate of infusion for the secondary fluid, said microprocessor means further accumulating the number of activations of said metering unit to determine the quantity of fluid metered into said delivery line, said microprocessor means directing said drive unit to activate said metering unit to meter fluid to said delivery line at a rate corresponding to the preselected rate of infusion of the primary fluid upon sensing the metering of a quantity of fluid corresponding to the preselected quantity of secondary fluid to be infused, said microprocessor means directing said drive unit to prevent further activation of said metering unit when said microprocessor means measures a quantity of fluid metered into said delivery line at the rate corresponding to the preselected rate of infusion of the primary fluid corresponding to the preselected quantity of primary fluid to be infused.

12. The apparatus of claim 11 wherein said metering unit comprises:
a metering chamber defined between first and second chamber walls;
first and second inlet tubes connected through the first and second chamber walls respectively;
first and second outlet tubes connected through the first and second chamber walls respectively;
valve means for selectively opening and closing said inlet and outlet tubes such that fluid flow is allowed alternatively in both of said first inlet tube and said second outlet tube and in both of said second inlet tube and said first outlet tube, said first and second inlet tubes being connected to said connector and said first and second outlet tubes being connected to said delivery line; and
a pressure transmitting member formed as a membrane of flexible sheet material extending between the chamber walls to define first and second compartments between the first and second chamber walls respectively and said pressure transmitting member, said pressure transmitting member being movable between the first and second chamber walls to simultaneously and alternately fill and empty said first and second compartments, said drive unit activating said valve means to permit fluid flow from said connector through one of said inlet tubes to the associated compartment, the fluid flowing into the compartment acting against said pressure transmitting member to urge fluid in the other compartment therefrom through the associated outlet tube into said delivery line, each activation of said valve means metering a predetermined volume of fluid into said delivery line.

13. The apparatus of claim 11 wherein said metering unit comprises:
first and second halves adapted to be secured in facing relation, each of said halves being constructed to form a reservoir portion, entry and exit channels extending from the reservoir portion and entry and exit port sections, the entry and exit channels and entry and exit port sections being interconnected by entry and exit orifices, respectively, the reservoir portions of each half forming a reservoir and said entry and exit port sections forming entry and exit ports, respectively, when said halves are secured in facing relation, the entry port being connected to said connector and the exit port being connected to said delivery line;
a flexible diaphragm means for positioning between said first and second halves when secured in facing relation to divide the reservoir into first and second compartments;
first entry valve means and first exit valve means for attachment to said first half, said first entry and exit valve means being movable from an open position permitting fluid flow through the entry and exit orifices, respectively to a closed position to prevent flow through the entry and exit orifices, respectively;
second entry valve means and second exit valve means for attachment to said second half, said second entry and exit valve means being movable from an open position permitting fluid flow through the entry and exit orifices, respectively to a closed position to prevent fluid flow through the entry and exit orifices, respectively;
activating means for alternately opening and closing each of said valves, said drive unit activating said metering unit by directing said activating means to change the positions of each of said valves, said first entry valve means and said second exit valve means simultaneously being opened and closed and said second entry valve means and said first exit valve means being simultaneously opened and closed to positions opposite said first entry valve means and said second exit valve means; and fluid entering said entry port flowing through the entry orifice and entry channel of said first half into the first compartment when said first entry valve means is open, the fluid entering said entry port having sufficient pressure head to move said diaphragm means to force the fluid in the second compartment through the exit channel and exit orifice of said second half to the exit port, fluid entering said entry port flowing through the entry orifice and entry channel of said second half into the second compartment when said second entry valve means is open, fluid entering said entry port having sufficient pressure head to move said diaphragm means to force the fluid in the first compartment through the exit channel and exit orifice of said first half to the exit port, the fluid displaced from each of the first and second compartments having a predetermined volume.

14. A controller for metering primary and secondary fluids stored in primary and secondary containers, respectively, to a delivery line for infusion into a patient, the primary and secondary fluids flowing from the primary and secondary containers to a connector, the fluid flowing through the connector into the controller, said controller comprising:

input means for input by an operator of a preselected rate of infusion for each of the primary and secondary fluids and a preselected volume of the secondary fluid to be infused;

metering means for metering fluid from the connector into the delivery line, said metering means permitting fluid flow into the delivery line within a range of flow rates; and microprocessor means for communicating with said input means and said metering means, said microprocessor means for activating said metering means to meter fluid into the delivery line at a rate corresponding to the preselected rate for the secondary fluid until a preselected quantity of fluid has been metered through said metering means corresponding to the preselected volume of the secondary fluid to be infused, said microprocessor means subsequently for activating said metering means to meter fluid into said delivery line at a rate corresponding to the preselected rate for the primary fluid.

15. The controller of claim 14 wherein said metering means comprises:

at least one compartment for holding a predetermined volume of fluid;

an inlet tube extending from the connector to said compartment for filling said compartment with fluid from the containers;

an outlet tube extending from said compartment to the delivery line for permitting flow therethrough to the patient;

valve means for selectively opening and closing said inlet and outlet tubes such that fluid flow is allowed alternatively in said inlet and outlet tubes; and drive means activated by said microprocessor means for moving said valve means to permit a predetermined volume of fluid to flow into the compartment and moving said valve means to permit a predetermined volume of fluid to flow from said compartment for infusion into the patient upon each activation thereof, said microprocessor means controlling the frequency of activation to meter fluid into the delivery line at the preselected rate and accumulating the number of activations to determine the quantity of fluid metered into the delivery line.

16. The controller of claim 14 wherein said metering means comprises:

first and second halves adapted to be secured in facing relation, each of said halves being constructed to form a reservoir portion, entry and exit channels extending from the reservoir portion and entry and exit port sections, the entry and exit channels and entry and exit port sections being interconnected by entry and exit orifices, respectively, the reservoir portions of each half forming a reservoir and said entry and exit port sections forming entry and exit ports, respectively, when said halves are secured in facing relation, the entry port being connected to said primary and secondary containers and the exit port being connected to said delivery line;

a flexible diaphragm means for positioning between said first and second halves when secured in facing relation to divide the reservoir into first and second compartments;

first entry valve means and first exit valve means for attachment to said first half, said first entry and exit valve means being movable from an open position permitting fluid flow through the entry and exit orifices, respectively, to a closed position to prevent flow through the entry and exit orifices, respectively;

second entry valve means and second exit valve means for attachment to said second half, said second entry and exit valve means being movable from an open position permitting fluid flow through the entry and exit orifices, respectively, to a closed position to prevent fluid flow through the entry and exit orifices, respectively;

activating means for alternately opening and closing each of said valves, said microprocessor means activating said metering unit by directing said actuating means to change the positions of each of said valves, said first entry valve means and said second exit valve means simultaneously being opened and closed and said second entry valve means and said first exit valve means being simultaneously opened and closed to positions opposite said first entry valve means and said second exit valve means; and fluid entering said entry port flowing through the entry orifice and entry channel of said first half into the first compartment when said first entry valve means is open, the fluid entering said entry port having sufficient pressure head to move said diaphragm means to force the fluid in the second compartment through the exit channel and exit orifice of said second half to the exit port, fluid entering said entry port flowing through the entry orifice and entry channel of said second half into the second compartment when said second entry valve means is open, fluid entering said entry port having sufficient pressure head to move said diaphragm means to force the fluid in the first compartment through the exit channel and exit orifice of said first half to the exit port, the fluid displaced from each of the first and second compartments having a predetermined volume.

17. A controller for metering primary and secondary fluids from primary and secondary containers, respectively, to a delivery line for infusion into a patient, the secondary fluid initially flowing into a connector until the secondary container is substantially empty, and the primary fluid subsequently flowing into the connector, fluid flowing through the connector into the controller, said controller comprising:

an input control for input by an operator of a preselected rate and quantity to be infused for each of the primary and secondary fluids;

a metering unit for metering a known quantity of fluid from the connector into the delivery line upon each activation of said metering unit;

a drive unit for activating said metering unit, said drive unit having a range of speeds to permit variation of the flow of fluid into said delivery line; and microprocessor means communicating with said input control and said drive unit, said microprocessor means directing said drive unit to activate said metering unit to meter fluid into said delivery line at a rate corresponding to the preselected rate for the secondary fluid input into said input control, said microprocessor means sensing the number of activations of said metering unit to measure the quantity of fluid metered into said delivery line, said microprocessor means directing said drive unit to activate said metering unit to meter fluid into said delivery line at a rate corresponding to the preselected rate for the primary fluid upon measuring flow through said metering unit equal to the preselected quantity of secondary fluid to be infused into the patient, said microprocessor means directing said drive unit to stop activation of said metering unit when said microprocessor means measures a total flow through said metering unit equal to the combined preselected quantity of primary fluid and secondary fluid to be infused into the patient.

18. The controller of claim 17 wherein said metering unit comprises:

a metering chamber having first and second compartments formed therein;

first and second inlet tubes connected respectively to the first and second compartments;

first and second outlet tubes connected respectively to the first and second compartments;

valve means for selectively opening and closing each of said inlet and outlet tubes such that fluid flow is allowed alternately in both of said first inlet tube and said second outlet tube and in both of said second inlet tube and said first outlet tube, said inlet tubes being connected to the connector and said outlet tubes being connected to the delivery line; and a movable pressure transmitting member positioned between the first and second compartments in said metering chamber, said pressure transmitting member forming a movable portion of each of the compartments and being movable between two positions such that the two compartments are simultaneously and alternately filled and emptied, the movement of said pressure transmitting member displacing a predetermined and equal amount of fluid in moving between the two positions so that the amount of fluid displaced from each of the two compartments is equal, said drive unit operating said valve means to meter the fluid in one of the compartments into the delivery line upon each activation of said metering unit.

19. The controller of claim 17 wherein said metering unit comprises:

first and second halves adapted to be secured in facing relation, each of said halves being constructed to form a reservoir portion, entry and exit channels extending from the reservoir portion and entry and exit port sections, the entry and exit channels and entry and exit port sections being interconnected by entry and exit orifices, respectively, the reservoir portions of each half forming a reservoir and said entry and exit port sections forming entry and exit ports, respectively, when said halves are secured in facing relation, the entry port being connected to the connector containers and the exit port being connected to said delivery line;

a flexible diaphragm means for positioning between said first and second halves when secured in facing relation to divide the reservoir into first and second compartments;

first entry valve means and first exit valve means for attachment to said first half, said first entry and exit valve means being movable from an position permitting fluid flow through the entry and exit orifices, respectively, to a closed position to prevent flow through the entry and exit orifices, respectively;

second entry valve means and second exit valve means for attachment to said second half, said second entry and exit valve means being movable from an open position permitting fluid flow through the entry and exit orifices, respectively, to a closed position to prevent fluid flow through the entry and exit orifices, respectively;

activating means for alternately opening and closing each of said valves, said drive unit activating said metering unit by directing said activating means to change the positions of each of said valves, said first entry valve means and said second exit valve means simultaneously being opened and closed and said second entry valve means and said first exit valve means being simultaneously opened and closed to positions opposite said first entry valve means and said second exit valve means; and fluid entering said entry port flowing through the entry orifice and entry channel of said first half into the first compartment when said first entry valve means is open, the fluid entering said entry port having sufficient pressure head to move said diaphragm means to force the fluid in the second compartment through the exit channel and exit orifice of said second half to the exit port, fluid entering said entry port flowing through the entry orifice and entry channel of said second half into the second compartment when said second entry valve means is open, fluid entering said entry port having sufficient pressure head to move said diaphragm means to force the fluid in the first compartment through the exit channel and exit orifice of said first half to the exit port, the fluid displaced from each of the first and second compartments having a predetermined volume.

20. A controller for use in a fluid delivery system infusing primary and secondary fluids into a patient through a delivery line, said primary and secondary fluids being stored in primary and secondary containers, respectively, the secondary fluid being stored at a higher elevation than the primary fluid, the system further having fluid lines extending from each container to a connector combining fluid flow from the containers for entry into a controller, a check valve being positioned to initially permit flow of the secondary fluid into the connector until the secondary container is substantially empty and subsequently permitting flow of the primary fluid into the connector, said controller comprising:

input means for input by an operator of a preselected rate of infusion for each of the primary and secondary fluids and a preselected quantity of secondary fluid to be infused;

metering means for metering a known quantity of fluid from the connector into the delivery line upon each activation thereof; and microprocessor means communicating with said input means and said metering means, said microprocessor means initially activating said metering means in a continuous manner at a predetermined frequency to meter fluid into the delivery line at a rate corresponding to the preselected rate for the secondary fluid, said microprocessor means further accumulating the number of activations of said metering means to determine the quantity of fluid metered into the delivery line through said metering means, said microprocessor means subsequently activating said metering means at a frequency to meter fluid into the delivery line at a rate corresponding to the preselected rate for the primary fluid upon sensing the metering of a quantity of fluid into the delivery line corresponding to the preselected quantity of the secondary fluid to be infused, the metering of fluid into the delivery line being independent of the flow of fluid from either the primary or secondary container.

21. A controller for use in a fluid delivery system infusing primary and secondary fluids into a patient through a delivery line, said primary and secondary fluids being stored in primary and secondary containers, respectively, the stored secondary fluid being elevated above the stored primary fluid, the system having fluid delivery lines extending from each of the containers to a connector combining the fluid flow therefrom for entry into the controller, a check valve being positioned to initially permit flow of secondary fluid into the connector until the secondary container is substantially empty and subsequently permitting flow of the primary fluid into the connector, said controller comprising:

input means for input by an operator of a preselected rate of infusion for each of the primary and secondary fluids and a preselected quantity of secondary fluid to be infused;

metering means for metering fluid from the connector to the delivery line, said metering means comprising:

a metering chamber having first and second compartments;

first and second inlet tubes connected respectively to the first and second compartment;

first and second outlet tubes connected respectively to the first and second compartment;

rod means for reciprocation between each of said inlet and outlet tubes such that fluid flow is allowed alternatively in both of said first inlet tube and said second outlet tube and in both of said second inlet tube and said first outlet tube, said inlet tubes being connected to the connector and said outlet tubes being connected to the delivery line; and a movable pressure transmitting member positioned between the first and second compartments in said metering chamber, the pressure transmitting member forming a movable portion of each of the compartments and being movable between two positions such that the two compartments are simultaneously and alternately filled and emptied of a known volume of fluid, the fluid entering one compartment from the connector moving the pressure transmitting member between the two positions to displace the known quantity of fluid from the other compartment into the delivery line; and microprocessor means for communicating with said input means and said metering means, said microprocessor means activating said metering means, the activation of said metering means causing said rod means to reciprocate to discharge the known quantity of fluid into the delivery line, said microprocessor means activating said metering means at a frequency to meter fluid into the delivery line at a rate corresponding to the preselected rate for the secondary fluid, said microprocessor means further accumulating the number of activations of said metering means to determine the quantity of fluid metered into the delivery line until a quantity of fluid has been metered into the delivery line corresponding to the preselected quantity of the secondary fluid to be infused into the patient, said microprocessor means subsequently activating said metering means at a frequency to meter fluid into the delivery line at a rate corresponding to the preselected rate for the primary fluid, the metering of the fluid into the delivery line being determined by the flow of fluid through said metering means.

\* \* \* \* \*

UNITED STATES PATENT AND TRADEMARK OFFICE
CERTIFICATE OF CORRECTION

PATENT NO. : 4,391,598

DATED : July 5, 1983

INVENTOR(S) : Thomas C. Thompson

It is certified that error appears in the above—identified patent and that said Letters Patent is hereby corrected as shown below:

Abstract, line 14, change "amd" to --and--;

Column 1, line 29, after "either" insert --attached--;

Column 9, line 24, omit hyphen at end of line;

Claim 7; column 13, line 30, change "fro" to --for--;

Claim 19; column 20, line 24, between "an" and "position" insert --open--.

Signed and Sealed this

Thirteenth Day of September 1983

[SEAL]

Attest:

GERALD J. MOSSINGHOFF

*Attesting Officer*     *Commissioner of Patents and Trademarks*